(12) United States Patent
Ghosh et al.

(10) Patent No.: US 7,368,410 B2
(45) Date of Patent: May 6, 2008

(54) ZEOLITE CATALYST AND METHOD OF PREPARING AND USE OF ZEOLITE CATALYST

(75) Inventors: Ashim Kumar Ghosh, Houston, TX (US); Neeta Kulkarni, Houston, TX (US); Pamela Harvey, Missouri City, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 252 days.

(21) Appl. No.: 11/195,970

(22) Filed: Aug. 3, 2005

(65) Prior Publication Data

US 2007/0032690 A1 Feb. 8, 2007

(51) Int. Cl.
*B01J 29/06* (2006.01)
(52) U.S. Cl. .......................... 502/63; 502/64; 502/71; 502/77
(58) Field of Classification Search ................ 502/77, 502/63, 64, 71
See application file for complete search history.

(56) References Cited

U.S. PATENT DOCUMENTS

| | | | |
|---|---|---|---|
| 3,702,886 A | 11/1972 | Argauer et al. |
| 3,962,364 A | 6/1976 | Young |
| 3,965,207 A | 6/1976 | Weinstein |
| 4,115,424 A | 9/1978 | Unland et al. |
| 4,140,726 A | 2/1979 | Unland et al. |
| 4,152,364 A | 5/1979 | Chu |
| 4,250,345 A | 2/1981 | Chu |
| 4,278,827 A | 7/1981 | Chu et al. |
| 4,409,132 A | 10/1983 | Forbus et al. |
| RE31,919 E | 6/1985 | Butter et al. |
| 4,548,914 A | 10/1985 | Chu |
| 4,554,394 A | 11/1985 | Forbus et al. |
| 4,590,321 A | 5/1986 | Chu |
| 4,623,530 A | 11/1986 | Cullo et al. |
| 4,623,533 A | 11/1986 | Young |
| 4,638,106 A | 1/1987 | Pieters et al. |
| 4,665,251 A | 5/1987 | Chu |
| 4,670,616 A | 6/1987 | De Simone et al. |
| 4,673,767 A | 6/1987 | Nimry et al. |
| 4,694,114 A | 9/1987 | Chu et al. |
| 4,695,666 A | 9/1987 | Chao et al. |
| 4,695,667 A | 9/1987 | Sumitani et al. |
| 4,704,495 A | 11/1987 | Dessau |
| 4,716,135 A | 12/1987 | Chen |
| 4,721,827 A | 1/1988 | Cullo et al. |
| 4,727,209 A | 2/1988 | Chao |
| 4,746,763 A | 5/1988 | Kocal |
| 4,758,328 A | 7/1988 | Young |
| 4,761,513 A | 8/1988 | Steacy |
| 4,781,815 A | 11/1988 | Pellet et al. |
| 4,847,223 A | 7/1989 | Le Van Mao et al. |
| 4,861,930 A | 8/1989 | Cottrell et al. |
| 4,873,067 A | 10/1989 | Valyocsik et al. |
| 4,891,197 A | 1/1990 | Derouane et al. |
| 4,891,467 A | 1/1990 | Sikkenga |
| 4,902,406 A | 2/1990 | Valyocsik |
| 4,912,073 A | 3/1990 | Chu |
| 4,914,067 A | 4/1990 | Pellet et al. |
| 4,935,574 A | 6/1990 | D'Amore et al. |
| 4,962,255 A | 10/1990 | Fraenkel et al. |
| 4,973,399 A | 11/1990 | Green et al. |
| 4,973,781 A | 11/1990 | Valyocsik et al. |
| 4,980,052 A | 12/1990 | Green et al. |
| 5,041,402 A | 8/1991 | Casci et al. |
| 5,043,502 A | 8/1991 | Martindale et al. |
| 5,047,141 A | 9/1991 | Chu |
| 5,068,483 A | 11/1991 | Barthomeuf et al. |
| 5,094,995 A | 3/1992 | Butt et al. |
| 5,105,047 A | 4/1992 | Waller |
| 5,108,579 A | 4/1992 | Casci |
| 5,110,776 A | 5/1992 | Chitnis et al. |
| 5,124,299 A | 6/1992 | Waller |
| 5,171,921 A | 12/1992 | Gaffney et al. |
| 5,173,461 A | 12/1992 | Absil et al. |
| 5,178,748 A | 1/1993 | Casci et al. |
| 5,210,356 A | 5/1993 | Shamshoum et al. |
| 5,227,558 A | 7/1993 | Shamshoum et al. |
| 5,231,064 A | 7/1993 | Absil et al. |
| 5,233,102 A | 8/1993 | Butt et al. |
| 5,246,688 A | 9/1993 | Faust et al. |
| 5,248,841 A | 9/1993 | Young |
| 5,254,767 A | 10/1993 | Dwyer |
| 5,254,770 A | 10/1993 | Olson et al. |
| 5,294,332 A | 3/1994 | Klotz |
| 5,294,578 A | 3/1994 | Ho et al. |
| 5,315,033 A | 5/1994 | Butt et al. |
| 5,318,696 A | 6/1994 | Kowalski |
| 5,321,183 A | 6/1994 | Chang et al. |

(Continued)

*Primary Examiner*—Elizabeth D. Wood
(74) *Attorney, Agent, or Firm*—Grady K. Bergen; Jim D. Wheelington; Griggs Bergen LLP

(57) ABSTRACT

A zeolite catalyst is prepared by treating a zeolite with a phosphorus compound to form a phosphorus-treated zeolite. The phosphorus-treated zeolite is heated to a temperature of about 300° C. or higher and combined with an inorganic oxide binder material to form a zeolite-binder mixture. The zeolite-binder mixture is heated to a temperature of about 400° C. or higher to form a bound zeolite catalyst. The bound zeolite may exhibit at least two $^{31}$P MAS NMR peaks with maxima at from about 0 to about −55 ppm, with at least one peak having a maximum at from about −40 to about −50 ppm. Zeolites containing 10-oxygen ring pores that have been prepared in such a way may be used in aromatic alkylation by contacting the bound zeolite catalyst with an aromatic alkylation feed of an aromatic compound and an alkylating agent under reaction conditions suitable for aromatic alkylation.

32 Claims, 8 Drawing Sheets

U.S. PATENT DOCUMENTS

| | | |
|---|---|---|
| 5,336,478 A | 8/1994 | Dwyer et al. |
| 5,336,824 A | 8/1994 | Shamshoum et al. |
| 5,345,021 A | 9/1994 | Casci et al. |
| 5,348,643 A | 9/1994 | Absil et al. |
| 5,349,113 A | 9/1994 | Chang et al. |
| 5,365,003 A | 11/1994 | Chang et al. |
| 5,366,948 A | 11/1994 | Absil et al. |
| 5,367,100 A | 11/1994 | Gongwei et al. |
| 5,371,307 A | 12/1994 | Guth et al. |
| 5,378,670 A | 1/1995 | Kumar |
| 5,380,690 A | 1/1995 | Zhicheng et al. |
| 5,385,718 A | 1/1995 | Casci et al. |
| 5,387,732 A | 2/1995 | Shamshoum et al. |
| 5,399,336 A | 3/1995 | Guth et al. |
| 5,430,212 A | 7/1995 | Butt et al. |
| 5,430,213 A | 7/1995 | Hendriksen et al. |
| 5,446,234 A | 8/1995 | Casci et al. |
| 5,455,213 A | 10/1995 | Chang et al. |
| 5,456,821 A | 10/1995 | Absil et al. |
| 5,464,799 A | 11/1995 | Casci et al. |
| 5,475,179 A | 12/1995 | Chang et al. |
| 5,498,814 A | 3/1996 | Chang et al. |
| 5,503,818 A | 4/1996 | Nicolaides |
| 5,516,736 A | 5/1996 | Chang et al. |
| 5,523,510 A | 6/1996 | Pellet et al. |
| 5,534,239 A | 7/1996 | Fajula et al. |
| 5,536,894 A | 7/1996 | Degnan et al. |
| 5,541,146 A | 7/1996 | Chang et al. |
| 5,561,095 A | 10/1996 | Chen et al. |
| 5,563,310 A | 10/1996 | Chang et al. |
| 5,569,805 A | 10/1996 | Beck et al. |
| 5,571,768 A | 11/1996 | Chang et al. |
| 5,573,746 A | 11/1996 | Chen |
| 5,576,256 A | 11/1996 | Monque et al. |
| 5,607,888 A | 3/1997 | Chang et al. |
| 5,607,890 A | 3/1997 | Chen et al. |
| 5,646,314 A | 7/1997 | Crocco et al. |
| 5,648,580 A | 7/1997 | Chen et al. |
| 5,658,454 A | 8/1997 | Absil et al. |
| 5,675,047 A | 10/1997 | Beck et al. |
| 5,689,024 A | 11/1997 | Schmitt |
| 5,698,756 A | 12/1997 | Beck et al. |
| 5,780,563 A | 7/1998 | Chen et al. |
| 5,789,335 A | 8/1998 | Chen et al. |
| 5,811,613 A | 9/1998 | Bhat et al. |
| 5,833,840 A | 11/1998 | Absil et al. |
| 5,847,255 A | 12/1998 | Ghosh et al. |
| 5,902,919 A | 5/1999 | Chen et al. |
| 5,905,051 A | 5/1999 | Wu et al. |
| 5,907,073 A | 5/1999 | Ghosh |
| 5,922,922 A | 7/1999 | Harris et al. |
| 5,925,586 A | 7/1999 | Sun |
| 5,939,597 A | 8/1999 | Dessau et al. |
| 5,951,963 A | 9/1999 | He et al. |
| 5,952,535 A | 9/1999 | King et al. |
| 5,955,641 A | 9/1999 | Chen et al. |
| 5,990,031 A | 11/1999 | Ghosh |
| 5,994,603 A | 11/1999 | Mohr et al. |
| 6,034,283 A | 3/2000 | Ban et al. |
| 6,040,257 A | 3/2000 | Drake et al. |
| 6,046,128 A | 4/2000 | Kisen et al. |
| 6,047,544 A | 4/2000 | Yamamoto et al. |
| 6,048,816 A | 4/2000 | Brown et al. |
| 6,057,485 A | 5/2000 | Merrill et al. |
| 6,060,633 A | 5/2000 | Chen et al. |
| 6,074,975 A | 6/2000 | Yao et al. |
| 6,080,303 A | 6/2000 | Cao et al. |
| 6,080,698 A | 6/2000 | Zhang et al. |
| 6,083,865 A | 7/2000 | Drake et al. |
| 6,090,274 A | 7/2000 | Wu et al. |
| 6,090,991 A | 7/2000 | Butler et al. |
| 6,096,938 A | 8/2000 | Ghosh |
| 6,100,437 A | 8/2000 | Koehl et al. |
| 6,124,227 A | 9/2000 | Yao et al. |
| 6,150,293 A | 11/2000 | Verduijn et al. |
| 6,156,949 A | 12/2000 | Brown et al. |
| 6,160,191 A | 12/2000 | Smith et al. |
| 6,187,982 B1 | 2/2001 | Beck et al. |
| 6,211,104 B1 | 4/2001 | Shi et al. |
| 6,217,748 B1 | 4/2001 | Hatanaka et al. |
| 6,222,084 B1 | 4/2001 | Ghosh et al. |
| 6,251,263 B1 | 6/2001 | Hatanaka et al. |
| 6,255,243 B1 * | 7/2001 | Drake et al. ................ 502/68 |
| 6,268,305 B1 | 7/2001 | Butler et al. |
| 6,294,493 B1 | 9/2001 | Strohmaier et al. |
| 6,300,535 B1 | 10/2001 | van den Berge et al. |
| 6,306,790 B1 | 10/2001 | Rodriguez et al. |
| 6,317,421 B1 | 11/2001 | Wilhelmsson et al. |
| 6,342,153 B1 | 1/2002 | Guan et al. |
| 6,388,156 B1 | 5/2002 | Ou et al. |
| 6,395,664 B1 | 5/2002 | Boehner et al. |
| 6,399,530 B1 | 6/2002 | Chen et al. |
| 6,423,879 B1 | 7/2002 | Brown et al. |
| 6,444,610 B1 | 9/2002 | Yamamoto |
| 6,459,006 B1 | 10/2002 | Ou et al. |
| 6,469,095 B1 | 10/2002 | Gareiss et al. |
| 6,503,862 B1 | 1/2003 | Yamamoto |
| 6,504,072 B1 | 1/2003 | Brown et al. |
| 6,504,074 B2 | 1/2003 | Berduijn et al. |
| 6,506,954 B1 | 1/2003 | Brown et al. |
| 6,518,213 B1 | 2/2003 | Yamamoto et al. |
| 6,548,725 B2 | 4/2003 | Froment et al. |
| 6,566,293 B1 | 5/2003 | Vogt et al. |
| 6,589,901 B2 | 7/2003 | Yamamoto |
| 6,613,708 B1 | 9/2003 | Ou et al. |
| 6,613,951 B1 | 9/2003 | Brown et al. |
| 6,642,426 B1 | 11/2003 | Johnson et al. |
| 6,689,929 B2 | 2/2004 | Williams et al. |
| 6,699,811 B1 | 3/2004 | Mohr et al. |
| 6,723,297 B2 | 4/2004 | Chen et al. |
| 6,726,834 B2 | 4/2004 | Quesada et al. |
| 6,770,251 B2 | 8/2004 | Yoshikawa |
| 6,773,694 B1 | 8/2004 | Lesch et al. |
| 6,799,089 B2 | 9/2004 | Toulhoat |
| 6,811,684 B2 | 11/2004 | Mohr et al. |
| 6,812,181 B2 | 11/2004 | van der Berge et al. |
| 6,864,399 B2 | 3/2005 | Merrill et al. |
| 2003/0004383 A1 | 1/2003 | Brown et al. |
| 2005/0027151 A1 | 2/2005 | Ghosh et al. |
| 2005/0070749 A1 | 3/2005 | Ghosh et al. |
| 2005/0154242 A1 | 7/2005 | Ghosh et al. |
| 2005/0197245 A1 | 9/2005 | Ghosh et al. |
| 2005/0209492 A1 | 9/2005 | Ghosh et al. |
| 2005/0209494 A1 | 9/2005 | Ghosh et al. |
| 2005/0240070 A1 | 10/2005 | Ghosh et al. |
| 2005/0277795 A1 | 12/2005 | Ghosh et al. |

* cited by examiner

ZEOLITE CATALYST AND METHOD OF PREPARING AND USE OF ZEOLITE CATALYST

TECHNICAL FIELD

The invention relates generally to the alkylation of aromatic compounds and catalysts used for such reactions and their preparation.

BACKGROUND

Para-xylene is a valuable substituted aromatic compound because of its great demand for its oxidation to terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene. Toluene methylation has been known to occur over acidic catalyst, particularly over zeolite or zeolite-type catalyst. In particular, ZSM-5-type zeolite, zeolite Beta and silicaaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction below.

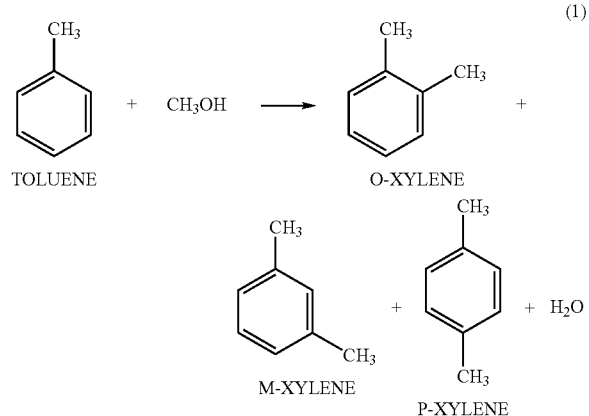

Thermodynamic equilibrium compositions of o-, m-, and p-xylenes may be around 25, 50 and 25 mole %, respectively, at a reaction temperature of about 500° C. Such toluene methylation may occur over a wide range of temperatures, however. Byproducts such as C9+ and other aromatic products can be produced by secondary alkylation of the xylene product.

Para-xylene can be separated from mixed xylenes by a cycle of adsorption and isomerization. Such cycle may have to be repeated several times because of the low isomeric concentration in the equilibrium mixture. A high purity grade (99+%) p-xylene is desirable for its oxidation to terephthalic acid. The production cost for such a high purity grade p-xylene can be very high, however. A different method that employs crystallization techniques can be used and may be less expensive where the concentration of p-xylene is around 80% or higher in the initial xylene product. Thus, higher than equilibrium concentrations of p-xylene may be desirable.

A significantly higher amount of p-xylene can be obtained in toluene methylation reaction if the catalyst has shape selective properties. Shape selective properties can be obtained in modified zeolite catalysts by narrowing zeolite pore opening size, inactivation of the external surface of the zeolite or controlling zeolite acidity. Toluene methylation may occur over modified ZSM-5 or ZSM-5-type zeolite catalyst giving xylene products containing significantly greater amounts of p-xylene than the thermodynamic concentration.

Unfortunately, there are a number of technical hurdles for toluene methylation to be commercially successful and improvements are needed. Among these are fast catalyst deactivation and low methanol selectivity.

BRIEF DESCRIPTION OF THE DRAWINGS

For a more complete understanding of the present invention, reference is now made to the following descriptions taken in conjunction with the accompanying figures, in which.

DETAILED DESCRIPTION

Figure 1:
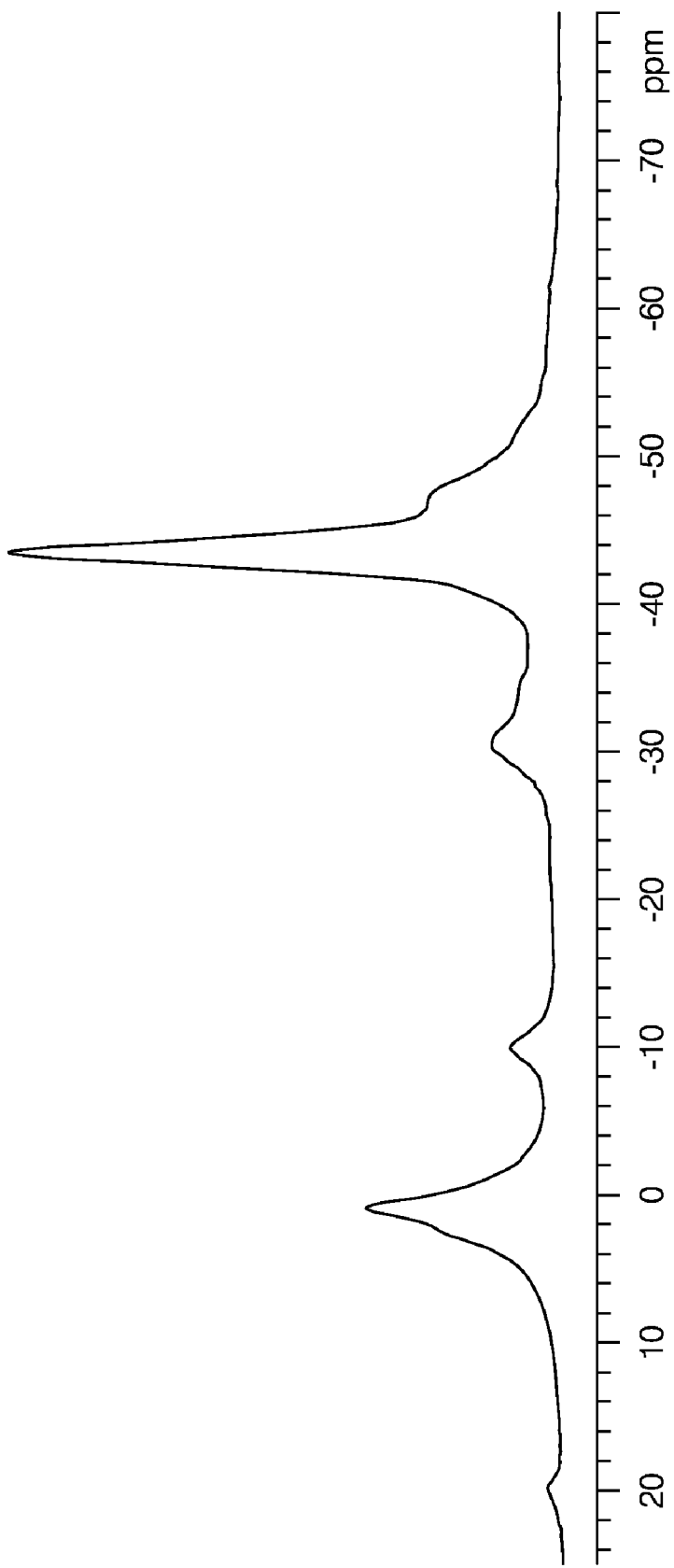
FIG. 1 shows $^{31}$P MAS-NMR spectrum for phosphorus-modified ZSM-5 zeolite Catalyst A.

ZSM-5 zeolite is one of the most versatile catalysts used in hydrocarbon conversions. It is a porous material containing intersecting two-dimensional pore structure with 10-membered oxygen rings. Zeolite materials with such 10-membered oxygen ring pore structures are often classified as medium-pore zeolites. Modification of ZSM-5-type zeolite catalysts with phosphorus-containing compounds has been shown to provide shape selective properties to the catalyst, yielding significantly greater amounts of p-xylene than the thermodynamic equilibrium value when used in toluene methylation compared to unmodified catalysts. Such modification has been shown to provide selectivity for p-xylenes of greater than 80%. Although such phosphorus-treated ZSM-5 catalysts may have a high selectivity for p-xylene, they tend to deactivate at a very fast rate; for example, the catalyst may lose greater than 50% of its initial activity within a day. This may possibly be due to coke deposition on the catalyst.

As used herein, the expression "ZSM-5-type" is meant to refer to those zeolites that are isostructurally the same as ZSM-5 zeolites. Additionally, the expressions "ZSM-5" and "ZSM-5-type" may also be used herein interchangeably to encompass one another and should not be construed in a limiting sense. As used herein, catalytic activity can be expressed as the % moles of the toluene converted with respect to the moles of toluene fed and can be defined by the following formulas:

$$\text{Mole \% Toluene Conversion} = [(T_i - T_o)/T_i] \times 100 \quad (2)$$

where, $T_i$ is the number of moles of toluene fed and $T_o$ is the number of moles toluene unreacted. As used herein, selectivity for mixed xylenes may be expressed as:

$$\text{Mole \% Mixed Xylene Selectivity} = [X_{tx}/(T_i - T_o)] \times 100 \quad (3)$$

where, $X_{tx}$ is the number of moles of mixed (o-, m- or p-) xylenes in the product. As used herein, selectivity for p-xylene may be expressed as:

$$\text{Mole \% p-Xylene Selectivity} = (X_p/X_{tx}) \times 100 \quad (4)$$

where, $X_p$ is the number of moles of p-xylene. As used herein, methanol conversion may be expressed as:

$$\text{Mole \% Methanol Conversion} = [(M_i - M_o)/M_i] \times 100 \quad (5)$$

where, $M_i$ is the number of moles of methanol fed and $M_o$ is the number of moles methanol unreacted. As used herein, methanol selectivity for toluene methylation may be expressed as:

$$\text{Mole \% Methanol Selectivity} = [X_{tx}/(M_i - M_o)] \times 100 \quad (6)$$

where, $X_{tx}$ is the number of moles of mixed (o-, m- or p-) xylenes, $M_i$ is the number of moles of methanol fed and $M_o$ is the number of moles of unreacted methanol.

The ZSM-5 zeolite catalysts and their preparation are described in U.S. Pat. No. 3,702,886, which is herein incorporated by reference. In the present invention, the ZSM-5 zeolite catalyst may include those having a silica/alumina molar ratio of 200 or higher, more particularly from about 250 to about 500 prior to modification. The starting ZSM-5 may be an $NH_4^+$ or $H^+$ form and may contain traces of other cations.

The ZSM-5 may be modified by treating with phosphorus-containing compounds. Such phosphorus-containing compounds may include, but are not limited to, phosphonic, phosphinous, phosphorus and phosphoric acids, salts and esters of such acids and phosphorous halides. In particular, phosphoric acid ($H_3PO_4$) and ammonium hydrogen phosphate (($NH_4)_2HPO_4$) may be used as the phosphorus-containing compound to provide a catalyst for toluene methylation with shape selective properties to provide increased p-xylene selectivity. Such modified catalysts may contain phosphorus (P) in an amount of from about 0.01 to about 0.15 g P/g zeolite, more particularly from about 0.02 to about 0.13 g P/g zeolite, and more particularly from about 0.07 g P/g zeolite to about 0.12 g P/g zeolite, and still more particularly from about 0.09 g P/g zeolite to about 0.11 g P/g zeolite. After phosphorus treatment, the phosphorus-treated zeolite may be dried.

It has been discovered that increased para-selectivity may be achieved in aromatic alkylation, particularly for toluene alkylation, when the P-modified zeolite is heated at 300° C. or higher after phosphorus treatment, and is then subsequently bound with a suitable binder, as is discussed later on. This heating may result in the formation of various phosphorus species within the zeolite. Such heating may also facilitate drying of the catalyst after the phosphorus treatment. Temperatures of 300° C., 400° C. or more are particularly useful in providing such increased para-selectivity. A suitable range for such heating subsequent to phosphorus treatment is from about 300° C. to about 600° C. Such heating may be carried out for 0.5 hour or more.

It has been further discovered that combining the P-treated ZSM-5 (P/ZSM-5) with a suitable binder after the initial heating step, as discussed above, may further increase product selectivity in aromatic alkylation. In particular, the P/ZSM-5 when heated and then bound with a suitable binder the catalyst may provide an increased selectivity for para-xylene by at least 5% compared to the same catalyst unbound when used in toluene methylation under similar conditions. Suitable binder materials may include inorganic oxide materials. Examples of such materials include alumina, clay, aluminum phosphate and silica-alumina. In particular, a binder of alumina or clay or their combinations are particularly useful. The bound catalyst may contain from about 1% to about 99% by total weight of bound catalyst, more particularly from about 10% to about 50% binder by total weight of bound catalyst.

To form the bound catalyst, the binder material may be combined with the phosphorus-treated zeolite to form an extrudable mixture. The P-treated zeolite bound with the binder may be calcined or heated at a temperature of 400° C. or higher, more particularly at a temperature between 500° C. and 700° C. Such heating may be carried out for 0.5 hours or more to form the bound catalyst. It has been discovered that heating the P-treated ZSM-5 at a temperature of about 300° C. or higher and then binding the zeolite with a suitable binder, as described herein, may result in the bound zeolite exhibiting multiple P-species, as shown by $^{31}P$ MAS NMR peaks.

In particular, the bound zeolite catalyst may exhibit at least two peaks having maxima at from about 0 ppm to about −55 ppm. More particularly, the bound zeolite catalyst may exhibit a $^{31}P$ MAS NMR peak having a maximum at from about 0 ppm to about −25 ppm, more particularly at from about −5 ppm to about −20 ppm, and another with a maximum at from about −40 ppm to about −50 ppm. Such peaks are an indication of various phosphorus species. In particular, a $^{31}P$ MAS NMR peak with maximum of about −44 ppm may be indicative of polyphosphate species. A peak with a maximum at from about 0 ppm to about −25 ppm may be indicative of phosphorus bound by extra-framework aluminum or amorphous alumina. Aluminophosphates ($AlPO_4$) and silicoaluminophosphates (SAPO) may be indicated by a peak with a maximum at around −28 ppm to about −35 ppm. Free phosphates may be indicated by a peak with a maximum at around 0 ppm.

This is in contrast to a bound P-modified zeolite catalyst that has been calcined or heated at the same temperature, but where the unbound P-modified zeolite precursor has not undergone heating at a temperature of 300° C. or more. Such bound P-modified zeolite catalysts have been shown to exhibit only a single $^{31}P$ MAS NMR peak. This indicates a difference in the interaction between the binder and the phosphorus species that is dependent upon the heating temperature of the unbound P-modified zeolite precursor.

The P-modified ZSM-5 catalyst, bound or unbound, may be mildly steamed at a temperature of 300° C. or lower before using the catalyst in any reaction. The steaming can be carried out in-situ or ex-situ of the reactor. The use of catalyst steaming at mild temperatures is described in co-pending U.S. patent application Ser. No. 11/122,919, filed May 5, 2005, entitled "Hydrothermal Treatment of Phosphorus-Modified Zeolite Catalysts," which is herein incorporated by reference.

The P-modified ZSM-5 catalyst, bound or unbound, may be contacted with an appropriate feed of an aromatic hydrocarbon and an alkylating agent under alkylation reaction conditions to carry out aromatic alkylation. The catalyst has particular application for use in toluene methylation utilizing a toluene/methanol feed. A gas cofeed may also be used. The cofeed gas may include hydrogen or an inert gas. As used herein, the expression "alklyation feed" is meant to encompass the aromatic compound and the alkylating agent. As used herein, the expression "methylation feed" is meant to encompass the feed of toluene and methanol.

In addition to any cofeed gas, water that may be in the form of steam, may also be introduced into the reactor as cofeed along with the alkylation feed. The water or steam used for the methylation reaction may be introduced with or without hydrogen or inert gas as cofeed with the alkylation feed to the reactor during the start up of the alkylation reaction, or it may be introduced subsequent to initial start up. In either case, liquid water may be added and vaporized prior to its mixing with cofeed gas (if any) and the alkylation feed. The use of water cofeed is described in U.S. Patent App. Publication No. US2005/0070749 A1, published Mar. 31, 2005, and entitled "Toluene Methylation Process," which is herein incorporated by reference.

The reactor pressure for toluene methylation or other aromatic alkylation may vary, but typically ranges from about 10 to about 1000 psig. Reactor temperatures may vary, but typically range from about 400 to about 700° C. Upon introduction of feed into the reactor, the catalyst bed temperature may be adjusted to a selected reaction temperature to effect a desired conversion. The temperature may be increased gradually at a rate of from about 1° C./min to about 10° C./min to provide the desired final reactor temperature. As used in the examples, reactor temperature refers to the temperature as measured at the inlet of catalyst bed of the reactor.

The reaction may be carried out in a variety of different reactors that are commonly used for carrying out aromatic alkylation reactions. Single or multiple reactors in series and/or parallel are suitable for carrying out the aromatic alkylation.

The P-modified ZSM-5 zeolite catalyst, as described herein, has particular application for use in toluene methylation for preparing a xylene product from a feed of toluene and methanol. The catalyst provides increased selectivity for p-xylene when used in toluene methylation. In particular, the catalyst may provide greater than 85%, 90% or 95% paraxylene selectivity when used in toluene methylation. Additionally, in certain instances, greater than 95% of total xylene selectivity may be achieved.

Additionally, the P/ZSM-5 catalyst described herein, bound or unbound, may provide steady catalyst activity and selectivity for toluene methylation over periods of 25 days, 30 days, 60 days or more under appropriate reaction conditions. In carrying out such reactions for steady catalyst performance, the catalyst may be contacted with a methylation feed and gas cofeed at a suitable temperature to give a desired toluene conversion. In the examples discussed below, the desired toluene conversion was 63% of theoretical maximum toluene conversion using a methylation feed containing a toluene/methanol molar ratio of about 4.5. The reaction was carried out at a constant reactor temperature over the test period.

The following examples better serve to illustrate the invention.

EXAMPLES

Catalyst A

A binder-free, P-modified ZSM-5 (P/ZSM-5) was prepared. The starting zeolite powder was an $NH_4$-ZSM-5 powder having $SiO_2/Al_2O_3$ mole ratio of 280. A slurry containing 700 g of $NH_4$-ZSM-5 zeolite and 700 ml of water was prepared in a 2-L beaker. The beaker was placed on a hot plate and the zeolite slurry was stirred using a mechanical (overhead) stirrer with 250-300 rpm. The temperature of the slurry was slowly raised to about 80-85° C. A phosphoric acid solution containing 319 g of phosphoric acid (Aldrich, 85 wt % in aqueous) was slowly added to the slurry. The slurry temperature was further increased to between 95-100° C. and heating was continued until all liquid was evaporated. The phosphoric-acid modified zeolite was then heated in a convection oven in air at the following temperature program: 90° C. to 120° C. for three hours, at 340° C. to 360° C. for three hours and at 510° C. to 530° C. under air for 10 hours. The resulting heat-treated zeolite (Catalyst A) was then crushed and sized using 20 and 40 mesh screens for catalytic reaction or sieved through 80 mesh screen for binding the zeolite with a binder.

Catalyst A was analyzed for Si, Al and P by X-ray fluorescence (XRF), and for BET surface area and total pore volume by $N_2$ adsorption. As shown in Table 1, Catalyst A contained 35.73 wt % Si, 0.28 wt % Al and 9.01 wt % P, and had a BET surface area of 160 m²/g and total pore volume of 0.12 ml/g. The X-ray diffraction pattern for Catalyst A was recorded on a Philips (X'Pert model) diffractometer over a range of 5-55° at a scan rate 2° per minute using CuKα1 radiation. The results are presented in Table 2.

TABLE 1

| Elemental Analysis, wt % | | | $N_2$ Adsorption | | |
|---|---|---|---|---|---|
| Si | Al | P | SA, m²/g | PV, ml/g | $^{31}$P MAS NMR |
| 35.73 | 0.28 | 9.01 | 160 | 0.12 | See spectrum FIG. 1 |

TABLE 2

Powder XRD Intensity*

| d-spacing [A] | Intensity |
|---|---|
| 11.09 | 100 |
| 10.00 | 55 |
| 9.88 | 42 |
| 9.68 | 17 |
| 8.02 | 8 |
| 6.68 | 7 |
| 6.33 | 8 |
| 5.98 | 16 |
| 5.69 | 7 |
| 5.56 | 9 |
| 4.25 | 9 |
| 4.00 | 6 |
| 3.84 | 50 |
| 3.81 | 31 |
| 3.71 | 27 |
| 3.64 | 10 |
| 3.52 | 22 |
| 2.98 | 8 |
| 2.78 | 5 |

*Intensities shown are scaled in arbitrary units so that most intense peak is 100.

Solid state Magic Angle Spinning (MAS) NMR spectra were recorded on Catalyst A with 400 MHz spectrometer ($^{27}$Al at 104.5 MHz) at room temperature ($^{27}$Al MAS NMR). Samples were packed in silicon nitride rotors ($Si_3N_4$) and spun at 13 to KHz sample spinning (about 800000 rpm). A 10 degree tip and recycle delay of 0.5 s were used to avoid saturation. About 4000 to 10000 scans were accumulated to signal average and improve signal/noise ratio. Proton decoupling was not employed. All spectra were referenced to aluminum chloride hexahydrate (run separately in a tube) at 0.0 ppm on the chemical shift scale. This leads to an internal reference of 104.85 ppm on the aluminum nitride (small impurity in the silicon nitride rotors) peak. The Catalyst A sample shows a weak peak at 55-50 ppm region assigned to structural tetrahedral aluminum. The tetrahedral aluminum peak is severely distorted, indicating the presence of nested silanols caused by holes in the structure upon removal of some of the framework aluminum. The adjacent peak (30-40 ppm) peak is due to severely distorted but still in the framework aluminum atoms probably either in the 3 or 5 coordination with oxygens. The biggest peak in the spectrum at −14 ppm is from octahedrally coordinated aluminum atoms that are formed when tetrahedrally coordinated framework aluminum is removed from the zeolite framework by the phosphate modification process as mentioned above.

Solid state Magic Angle Spinning (MAS) NMR spectra were recorded on Catalyst A with 400 MHz spectrometer ($^{31}$at 161.7 MHz) at room temperature ($^{31}$P MAS NMR). Samples were packed in silicon nitride rotors ($Si_3N_4$) and spun at 13 to KHz sample spinning (about 800000 rpm). A 30 degree tip and recycle delay of 15 s were used to avoid saturation. About 4000 to 10000 scans were accumulated to signal average and improve signal/noise ratio. Proton decoupling was not employed. All spectra were doubly referenced to tetramethyl diphosphine disulphide at 37.8 ppm and 85% phosphoric acid (run separately in a tube) at 0.0 ppm on the chemical shift scale.

FIG. 1 illustrates $^{31}$P MAS NMR spectrum for a P/ZSM-5 zeolite (Catalyst A). The $^{31}$P MAS NMR spectrum for Catalyst A shows peaks at 0, −11, −31 and −44 ppm attributed to various P-species such as free phosphorus and phosphorus bonded (via oxygen) to Si and Al.

Catalyst B

Heat-treated, P-modified ZSM-5 (described as Catalyst A earlier) was bound with 20 wt % alumina binder. 19.18 gm of alumina (pseudobohemite type, available from Alcoa, HiQ-40 grade) was peptized with mineral acid (e.g., $HNO_3$) and then mixed with 57.44 gm of P/ZSM-5 zeolite powder (80 mesh). Water was spray added to make a soft paste. The catalyst paste was calcined or heated (as irregular chunks or formed in a cylindrical shape) at 510° C. to 530° C. using the same temperature profile as described for Catalyst A above. The resulting Catalyst B was crushed and sized using 20 and 40 mesh screens for catalytic test.

Catalyst C

Heat-treated, P-modified ZSM-5 (earlier described as Catalyst A) was bound with 20% silica binder. 8.19 gm of Aerosil-200 was mixed with 5.05 gm of Ludox-HS-40 (Colloidal Silica) in which 20.0 ml of 0.2 N $NH_4OH$ was added slowly with stirring. 20.02 gm of P/ZSM-5 powder (80 mesh) was added to the silica mixture and stirred well. Water was sprayed to make soft paste and the paste was calcined at 510° C. to 530° C. using the same temperature profile as described for catalyst A above. The resulting Catalyst C was crushed and sized using 20 and 40 mesh screens for catalytic tests.

Catalyst D

Catalyst A was bound with 20% aluminum phosphate. Catalyst A was bound with aluminum phosphate, available from Aldrich Chemicals, as a binder following the same procedure as described for Catalyst B. The resulting Catalyst D was crushed and sized using 20 and 40 mesh screens for catalytic test.

Catalyst E

Catalyst A was bound with 20% kaolin. P/ZSM-5 was bound with kaolin as binder following the same procedure as described for Catalyst B. Kaolin (aluminum silicate hydroxide), available from Aldrich Chemicals, was used. The resulting Catalyst E was crushed and sized using 20 and 40 mesh screens for catalytic test.

Examples 1-5

In Examples 1-5, Catalysts A-E were used in toluene methylation. The reactions were each carried out in a fixed bed, continuous flow type reactor. In each case, a catalyst charge of 5.4 ml (catalyst size: 20-40 mesh) was loaded in the reactor. The catalyst was dried by slowly raising the catalyst bed temperature (about 5° C./min) to 200° C. under hydrogen flow (50 cc/min) for at least one hour. The catalyst was steamed by introducing water vapor (2.2 mmole/min) with a carrier gas of $H_2$ (459 cc/min) at 200° C. overnight. A premixed toluene and methanol feed (molar ratio 4.5) was added to the reactor at 200° C. and the catalyst bed inlet temperature was increased to about 550° C. The liquid hourly space velocity (LHSV) (based on methylation feed) was maintained at about 2 hr$^{-1}$ and a cofeed $H_2$ gas was fed and maintained to provide a $H_2$/methylation feed molar ratio of about 7-8. In addition, water was added to the reactor as cofeed and was vaporized prior to introduction to the reactor. The $H_2O$/methylation feed molar ratio was about 0.8 and the reactor pressure was about 20 psig. Reactor streams were analyzed to calculate conversion and selectivity. Liquid product stream analyses and conversion and selectivity for toluene methylation reaction over Catalysts A-E are shown in Table 3 below.

TABLE 3

| | Catalyst | | | | | | | | | |
|---|---|---|---|---|---|---|---|---|---|---|
| | A | | B | | C | | D | | E | |
| EXAMPLE | 1 | | 2 | | 3 | | 4 | | 5 | |
| Time on Stream, h | 28 | 118 | 24 | 125 | 22 | 124 | 30 | 150 | 25 | 131 |
| | | | Product Analysis, wt % | | | | | | | |
| Water | 20.6 | 20.3 | 20.9 | 21.5 | 19.2 | 18.8 | 19.3 | 19.2 | 20.2 | 19.6 |
| Methanol | 0.3 | 0.3 | 0.1 | 0.2 | 1.2 | 1.1 | 1.1 | 0.9 | 0.7 | 0.6 |
| Dimethylether | 0 | 0 | 0 | 0 | 0 | 0 | 0 | 0 | 0 | 0 |
| Benzene | 0 | 0 | 0 | 0 | 0 | 0 | 0 | 0 | 0 | 0 |

TABLE 3-continued

| EXAMPLE | Catalyst A 1 | | B 2 | | C 3 | | D 4 | | E 5 | |
|---|---|---|---|---|---|---|---|---|---|---|
| Toluene | 64.4 | 64.8 | 65.2 | 64.9 | 76.2 | 76.8 | 76.5 | 76.0 | 69.9 | 69.5 |
| Ethylbenzene | 0 | 0 | 0 | 0 | 0 | 0 | 0 | 0 | 0 | 0 |
| p-Xylene | 12.7 | 12.6 | 13.3 | 12.8 | 2.8 | 2.7 | 2.9 | 3.6 | 8.3 | 9.4 |
| m-Xylene | 0.9 | 0.9 | 0.2 | 0.2 | 0.3 | 0.2 | 0.1 | 0.1 | 0.4 | 0.4 |
| o-Xylene | 0.5 | 0.5 | 0.1 | 0.1 | 0.2 | 0.2 | 0.1 | 0.1 | 0.2 | 0.2 |
| Ethyltoluenes | 0.1 | 0.1 | 0.1 | 0.1 | 0 | 0 | 0 | 0 | 0 | 0 |
| Trimethylbenzenes | 0.4 | 0.4 | 0.1 | 0.1 | 0.1 | 0.1 | 0 | 0 | 0.2 | 0.2 |
| C10+ | 0 | 0 | 0 | 0 | 0 | 0 | 0 | 0 | 0 | 0 |
| Conversion/Selectivity, mole % | | | | | | | | | | |
| Toluene Conversion | 15.4 | 14.6 | 14.9 | 13.6 | 2.6 | 2.0 | 2.8 | 2.7 | 8.7 | 9.7 |
| Mixed Xylene Selectivity | 97.1 | 97.1 | 98.6 | 98.6 | 88.5 | 97.5 | 100 | 100 | 98.1 | 98.2 |
| p-Xylene Selectivity | 89.6 | 89.6 | 97.7 | 97.8 | 84.8 | 86.0 | 93.2 | 94.3 | 93.4 | 94.0 |
| Methanol Selectivity | 75.6 | 72.3 | 62.9 | 64.3 | 29.5 | 24.9 | 27.1 | 27.7 | 58.0 | 61.0 |

Examples 6-8

Catalyst F-H

Using the procedure described for Catalyst A, NH$_4$-ZSM-5 having a SiO$_2$/Al$_2$O$_3$ molar ratio of 280 was treated with H$_3$PO$_4$ acid. The H$_3$PO$_4$ acid treated ZSM-5 was then heated at 510-530° C. for approximately 10 hrs. Three alumina bound catalysts were made using the resulting P/ZSM-5 powder with 10 wt % alumina (Alcoa HiQ40) as binder and each was further calcined or heated at different maximum temperatures to form Catalysts F-H. Catalyst F was heated at a maximum temperature of 400° C. Catalyst G was heated at a maximum temperature of 510° C. Catalyst H was heated at a maximum temperature of 600° C. The catalysts were tested for toluene methylation using the conditions described in Examples 1-5. Table 4 shows the liquid product stream analysis and conversion and selectivity for Catalysts F-H for Examples 6-8.

TABLE 4

| EXAMPLE | Catalyst F 6 | | G 7 | | H 8 | |
|---|---|---|---|---|---|---|
| Time on Stream, h | 24 | 143 | 23 | 125 | 24 | 120 |
| Product Analysis, wt % | | | | | | |
| Water | 21.0 | 21.5 | 21.0 | 20.8 | 21.1 | 20.5 |
| Methanol | 0.1 | 0.1 | 0.1 | 0.2 | 0.1 | 0.2 |
| Dimethylether | 0 | 0 | 0 | 0 | 0 | 0 |
| Benzene | 0 | 0 | 0 | 0 | 0 | 0 |
| Toluene | 64.6 | 63.5 | 65.2 | 65.6 | 65.1 | 65.9 |
| Ethylbenzene | 0 | 0 | 0 | 0 | 0 | 0 |
| p-Xylene | 13.7 | 14.2 | 12.8 | 12.6 | 13.2 | 13.0 |
| m-Xylene | 0.3 | 0.3 | 0.4 | 0.4 | 0.2 | 0.2 |
| o-Xylene | 0.2 | 0.2 | 0.2 | 0.2 | 0.1 | 0.1 |
| Ethyltoluenes | 0.1 | 0.1 | 0.1 | 0.1 | 0.1 | 0.1 |
| Trimethylbenzenes | 0.2 | 0.2 | 0.2 | 0.2 | 0.1 | 0.1 |
| C10+ | 0 | 0 | 0 | 0 | 0 | 0 |
| Conversion/Selectivity, mole % | | | | | | |
| Toluene Conversion | 14.7 | 14.7 | 13.8 | 13.4 | 13.4 | 13.4 |
| Mixed Xylene Selectivity | 98.3 | 98.2 | 98.2 | 98.2 | 98.6 | 98.5 |
| p-Xylene Selectivity | 96.9 | 96.9 | 95.7 | 95.8 | 98.2 | 98.2 |
| Methanol Selectivity | 65.6 | 65.8 | 64.0 | 63.4 | 60.7 | 64.4 |

Examples 9-11

Catalysts I-K

Figure 2:
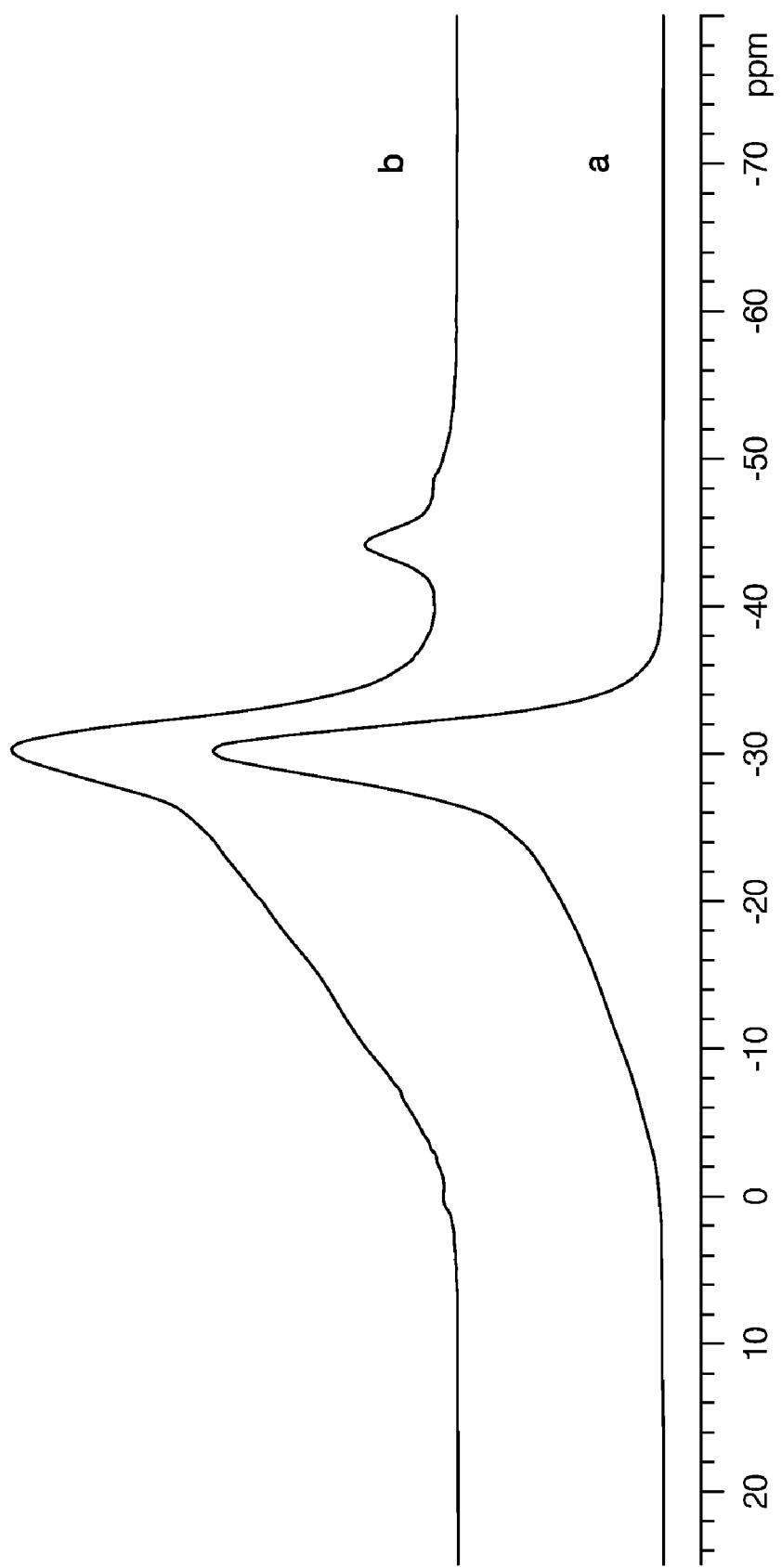
FIG. 2 shows $^{31}$P MAS-NMR spectra for Catalysts I (spectrum a) and K (spectrum b)

Using the procedure described for Catalyst A, NH$_4$-ZSM-5 having a SiO$_2$/Al$_2$O$_3$ molar ratio of 280 was treated with H$_3$PO$_4$ acid. The H$_3$PO$_4$ acid treated ZSM-5 was then heated at different temperatures of 90° C., 250° C. or 320° C. The heat-treated, P-modified ZSM-5 zeolite powder was then combined with 20 wt % alumina (Alcoa HiQ40) following the same procedure described for Catalyst B, and was calcined or heated at a maximum temperature of from 510 to 530° C. These bound catalysts, designated as Catalysts I, J and K, were tested for toluene methylation using the conditions described for Examples 1-5. The $^{31}$P MAS NMR spectra for Catalysts I and K are shown in FIG. 2. The $^{31}$P MAS NMR spectrum for Catalyst I shows only a single peak at around −30 ppm with a long tail (FIG. 2 spectrum a). As the heating temperature is increased for the P/ZSM-5 (used prior to binding with alumina) to about 300° C. or higher, the final bound catalyst may show additional peak(s), including a peak at around −44 ppm (see, for example, spectrum b of FIG. 2 and spectrum b of FIG. 3). Table 5 summarizes the initial heating temperature of the unbound P/ZSM-5 and catalytic test results obtained for bound Catalysts I-K. Also, the data for Catalyst B reproduced from Table 3 is presented in Table 5 for comparison. Those catalysts made from the P-modified ZSM-5 zeolite that were heated at a temperature of 300° C. or higher and then bound with a suitable binder showed 90% or higher p-xylene selectivity for toluene methylation.

TABLE 5

| | Catalyst | | | | | | | |
|---|---|---|---|---|---|---|---|---|
| | I | | J | | K | | B | |
| | P/ZSM-5 Heating Temp[1] | | | | | | | |
| | 90° C. | | 250° C. | | 320° C. | | 520° C. | |
| EXAMPLE | 9 | | 10 | | 12 | | 2 | |
| Time on Stream, h | 23 | 126 | 54 | 150 | 24 | 126 | 24 | 125 |
| Product Analysis, wt % | | | | | | | | |
| Water | 21.0 | 21.0 | 20.9 | 21.7 | 21.1 | 21.6 | 20.9 | 21.5 |
| Methanol | 0 | 0 | 0 | 0 | 0 | 0 | 0.1 | 0.2 |

TABLE 5-continued

| | Catalyst | | | | | | | |
|---|---|---|---|---|---|---|---|---|
| | I | | J | | K | | B | |
| | P/ZSM-5 Heating Temp[1] | | | | | | | |
| | 90° C. | | 250° C. | | 320° C. | | 520° C. | |
| EXAMPLE | 9 | | 10 | | 12 | | 2 | |
| Dimethylether | 0 | 0 | 0 | 0 | 0 | 0 | 0 | 0 |
| Benzene | 0.3 | 0.1 | 0.1 | 0.1 | 0.1 | 0 | 0 | 0 |
| Toluene | 63.4 | 63.0 | 63.8 | 62.3 | 65.8 | 64.0 | 65.2 | 64.9 |
| Ethylbenzene | 0 | 0 | 0 | 0 | 0 | 0 | 0 | 0 |
| p-Xylene | 12.1 | 13.3 | 12.5 | 13.1 | 12.7 | 14.0 | 13.3 | 12.8 |
| m-Xylene | 2.2 | 1.8 | 2.3 | 1.7 | 0.2 | 0.2 | 0.2 | 0.2 |
| o-Xylene | 0.8 | 0.7 | 0.1 | 0.7 | 0.1 | 0.1 | 0.1 | 0.1 |
| Ethyltoluenes | 0 | 0 | 0 | 0.1 | 0.1 | 0.1 | 0.1 | 0.1 |
| Trimethyl-benzenes | 0.2 | 0.3 | 0.3 | 0.3 | 0 | 0 | 0.1 | 0.1 |
| C10+ | 0 | 0 | 0 | 0 | 0 | 0 | 0 | 0 |
| | Conversion/Selectivity, mole % | | | | | | | |
| Toluene Conversion | 16.2 | 16.6 | 15.6 | 16.4 | 13.2 | 14.6 | 14.9 | 13.6 |
| Mixed Xylene Selectivity | 96.7 | 97.7 | 96.4 | 97.2 | 98.6 | 99.2 | 98.6 | 98.6 |
| p-Xylene Selectivity | 80.0 | 84.6 | 84.1 | 84.7 | 98.2 | 98.4 | 97.7 | 97.8 |
| Methanol Selectivity | 69.7 | 72.1 | 67.9 | 70.8 | 58.3 | 64.6 | 62.9 | 64.3 |

[1]Maximum temperature at which P/ZSM-5 was heated prior to binding with alumina.

For comparison purposes, the conversion and selectivity data shown in Table 5 was averaged, and those observed for Catalyst I were scaled to 1.00 and then were compared with other catalysts on a relative scale. As shown in Table 6, with the increase of the first heating temperature of the phosphorus-treated ZSM-5 prior to combining the zeolite with a binder, the p-xylene selectivity increased with a decrease in toluene conversion.

TABLE 6

| | Catalyst | | | |
|---|---|---|---|---|
| | I | J | K | B |
| P/ZSM-5 Heating Temperature, ° C.[1] | 90 | 250 | 320 | 520 |
| Relative Activity[2] | 1.00 | 0.98 | 0.85 | 0.87 |
| Relative Para-Selectivity[2] | 1.00 | 1.02 | 1.19 | 1.19 |

[1]Maximum temperature at which P/ZSM-5 was heated prior to binding with alumina.
[2]Average of two data points shown in Table 1 and 5 for the respective catalyst. Activity and selectivity observed on catalyst I were scaled to 1.00 and then compared with those obtained on other catalysts.

As can be seen, the P/ZSM-5 zeolite that was heated at a temperature of about 300° C. or above, and then bound with alumina followed by calcinations or heating at 500° C. above showed increased shape selectivity producing p-xylene selectively for toluene methylation. Higher activity with decreased p-selective catalyst can be achieved by heating the P/ZSM-5 at 300° C. or less and binding with alumina and calcining or heating at 500° C. or higher.

Examples 12-13

Catalyst L and M

Figure 3:
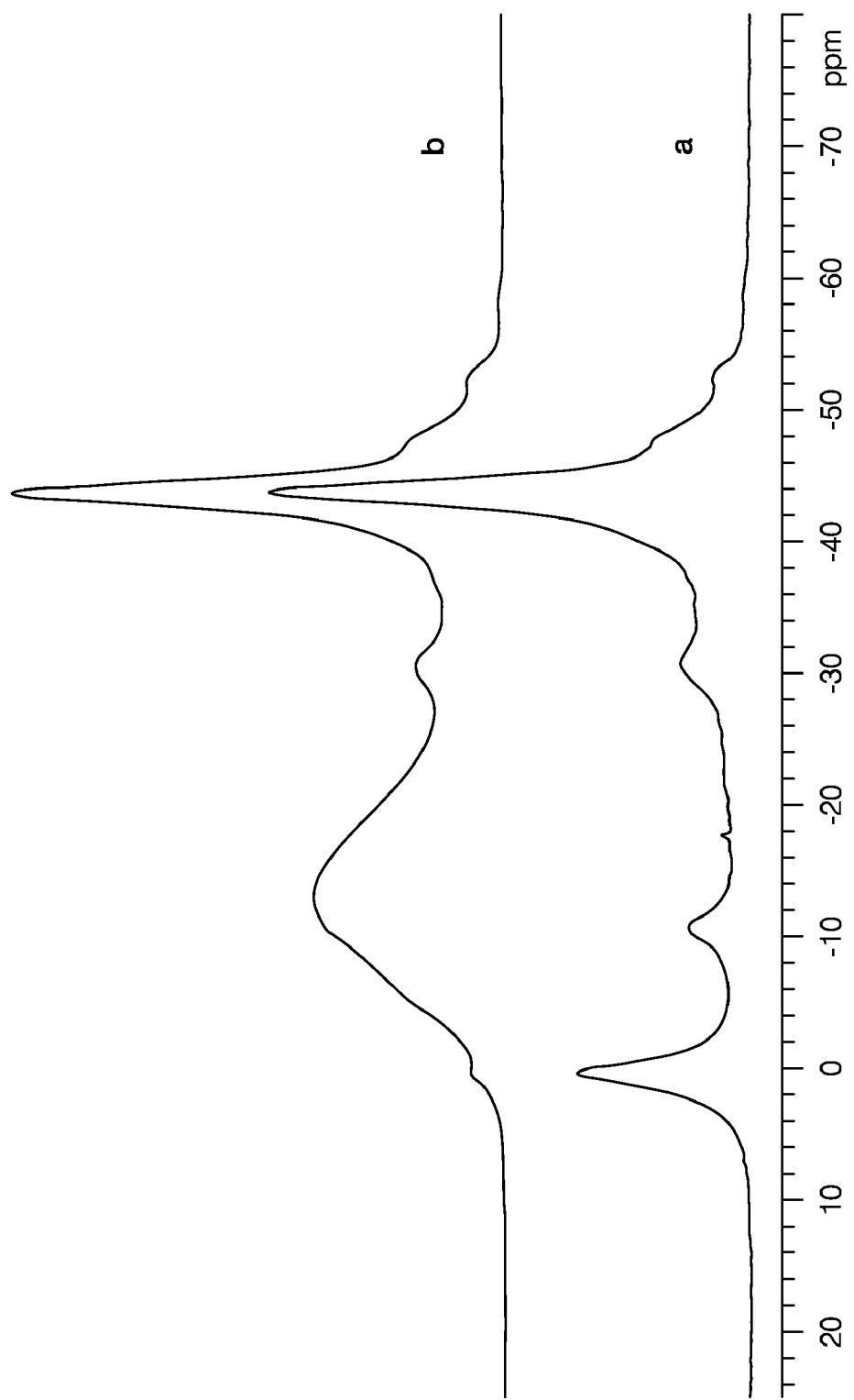
FIG. 3 shows $^{31}$P MAS-NMR spectra for a phosphorus-modified ZSM-5 zeolite (spectrum a) precursor used for preparing Catalysts L and M, and for an alumina bound phosphorus-modified ZSM-5 zeolite—Catalyst M (spectrum b)

Using the procedure described for Catalyst A, an NH4-ZSM-5 zeolite (SiO2/Al2O3 mole ratio 280) was treated with H3PO4 and then heated at a maximum temperature of 550° C. Analyses of the P-treated ZSM-5 zeolite powder, as was carried out for Catalyst A, are shown in Tables 7 and 8. The $^{31}$P MAS NMR of the P/ZSM-5 zeolite is shown in FIG. 3 (spectrum a). The P/ZSM-5 showed similar properties to those of Catalyst A. The P/ZSM-5 zeolite was bound with 20% alumina (pseudobohemite type) and extruded to make 1/16-inch cylindrical shape catalyst. Alcoa alumina grades HiQ-40 and HiQ-10 were used for Catalyst L and M, respectively. Catalysts L and M were calcined or heated at a maximum temperature between 510° C. and 530° C. FIG. 3 shows a $^{31}$P MAS NMR spectrum (spectrum b) for an alumina bound catalyst—Catalyst M. The $^{31}$P MAS NMR spectrum for Catalyst M shows two strong peaks at around −13 ppm (broad peak) and −44 ppm. This differs significantly from the $^{31}$P MAS NMR spectrum for Catalyst I, as shown in FIG. 2 (spectrum a).

TABLE 7

| Elemental Analysis, wt % | | | N2 Adsorption | | |
|---|---|---|---|---|---|
| Si | Al | P | SA, m2/g | PV, ml/g | $^{31}$P MAS NMR |
| 35.38 | 0.30 | 9.72 | 188 | 0.15 | See spectrum a in FIG. 3 |

TABLE 8

| Powder XRD Intensity* | |
|---|---|
| d-spacing [A] | Intensity |
| 11.08 | 100 |
| 9.99 | 54 |
| 9.89 | 46 |
| 9.70 | 17 |
| 8.01 | 6 |
| 6.54 | 7 |
| 6.33 | 9 |
| 5.98 | 16 |
| 5.70 | 6 |
| 5.55 | 8 |
| 4.25 | 6 |
| 4.00 | 7 |
| 3.84 | 57 |
| 3.80 | 27 |
| 3.71 | 28 |
| 3.64 | 11 |
| 3.53 | 18 |
| 2.98 | 10 |
| 2.78 | 6 |

*Intensities shown are scaled in arbitrary units so that most intense peak is 100.

Catalyst L and M were tested for toluene methylation. The reactor, catalyst charge, catalyst drying and steaming procedure were the same as described in Examples 1-5, and the reaction conditions were the same as in Examples 1-5. Reactor liquid product stream analysis and conversion and selectivity for Catalysts L and M are shown in Tables 9 and 10, respectively. Under the reaction conditions used for toluene methylation, Catalysts L and M showed initial 14% toluene conversion (63% of theoretical maximum) with greater than 98% mixed-xylene and 96% p-xylene selectivity.

TABLE 9

| Example | Catalyst L 12 | | | | | | |
|---|---|---|---|---|---|---|---|
| Time on Stream, h | 24 | 48 | 78 | 150 | 198 | 246 | 318 |
| Product Analysis, wt % | | | | | | | |
| Water | 20.6 | 20.9 | 22.0 | 20.5 | 20.8 | 20.0 | 19.8 |
| Methanol | 0 | 0 | 0.1 | 0.1 | 0.1 | 0.1 | 0.1 |
| Dimethylether | 0 | 0 | 0 | 0 | 0 | 0 | 0 |
| Benzene | 0 | 0 | 0 | 0 | 0 | 0 | 0 |
| Toluene | 65.5 | 65.1 | 63.9 | 65.9 | 65.6 | 66.1 | 66.4 |
| Ethylbenzene | 0 | 0 | 0 | 0 | 0 | 0 | 0 |
| p-Xylene | 13.1 | 13.2 | 13.3 | 12.8 | 12.8 | 13.1 | 13.0 |
| m-Xylene | 0.4 | 0.4 | 0.4 | 0.3 | 0.3 | 0.3 | 0.3 |
| o-Xylene | 0.1 | 0.1 | 0.2 | 0.1 | 0.1 | 0.2 | 0.2 |
| Ethyltoluenes | 0.1 | 0.1 | 0.1 | 0.1 | 0.1 | 0.1 | 0.1 |
| Trimethylbenzenes | 0.1 | 0.1 | 0.2 | 0.2 | 0 | 0.2 | 0.2 |
| C10+ | | | | | | | |
| Conversion/Selectivity, mole % | | | | | | | |
| Toluene Conversion | 14.0 | 14.2 | 14.3 | 13.3 | 13.4 | 13.7 | 13.5 |
| Mixed Xylene Selectivity | 98.4 | 98.4 | 98.3 | 98.3 | 98.4 | 98.3 | 98.3 |
| p-Xylene Selectivity | 96.2 | 96.2 | 96.3 | 96.3 | 96.3 | 96.5 | 96.5 |
| Methanol Selectivity | 62.3 | 63.1 | 64.7 | 61.8 | 62.0 | 63.0 | 61.8 |

TABLE 10

| Example | Catalyst M 13 | | | | | | |
|---|---|---|---|---|---|---|---|
| Time on Stream, h | 24 | 54 | 126 | 150 | 173 | 293 | 313 |
| Product Analysis, wt % | | | | | | | |
| Water | 20.3 | 20.5 | 19.9 | 19.9 | 21.2 | 20.4 | 20.4 |
| Methanol | 0.1 | 0.2 | 0.2 | 0.2 | 0.3 | 0.2 | 0.2 |
| Dimethylether | 0 | 0 | 0 | 0 | 0 | 0 | 0 |
| Benzene | 0 | 0 | 0 | 0 | 0 | 0 | 0 |
| Toluene | 66.0 | 65.4 | 65.9 | 65.8 | 64.6 | 65.5 | 65.8 |
| Ethylbenzene | 0 | 0 | 0 | 0 | 0 | 0 | 0 |
| p-Xylene | 12.9 | 13.2 | 13.3 | 13.4 | 13.2 | 13.1 | 12.8 |
| m-Xylene | 0.3 | 0.3 | 0.3 | 0.3 | 0.3 | 0.3 | 0.3 |
| o-Xylene | 0.2 | 0.2 | 0.2 | 0.2 | 0.2 | 0.2 | 0.2 |
| Ethyltoluenes | 0.1 | 0.1 | 0.1 | 0.1 | 0.1 | 0.1 | 0.1 |
| Trimethylbenzenes | 0.2 | 0.2 | 0.2 | 0.2 | 0.2 | 0.2 | 0.2 |
| C10+ | 0 | 0 | 0 | 0 | 0 | 0 | 0 |
| Conversion/Selectivity, mole % | | | | | | | |
| Toluene Conversion | 13.6 | 13.9 | 13.9 | 13.8 | 14.1 | 13.8 | 13.6 |
| Mixed Xylene Selectivity | 98.2 | 98.3 | 98.3 | 98.3 | 98.3 | 98.3 | 98.3 |
| p-Xylene Selectivity | 96.6 | 96.6 | 96.6 | 96.7 | 97.0 | 97.0 | 96.7 |
| Methanol Selectivity | 63.3 | 64.9 | 65.5 | 66.1 | 67.9 | 67.0 | 65.6 |

Example 14

Figure 4:
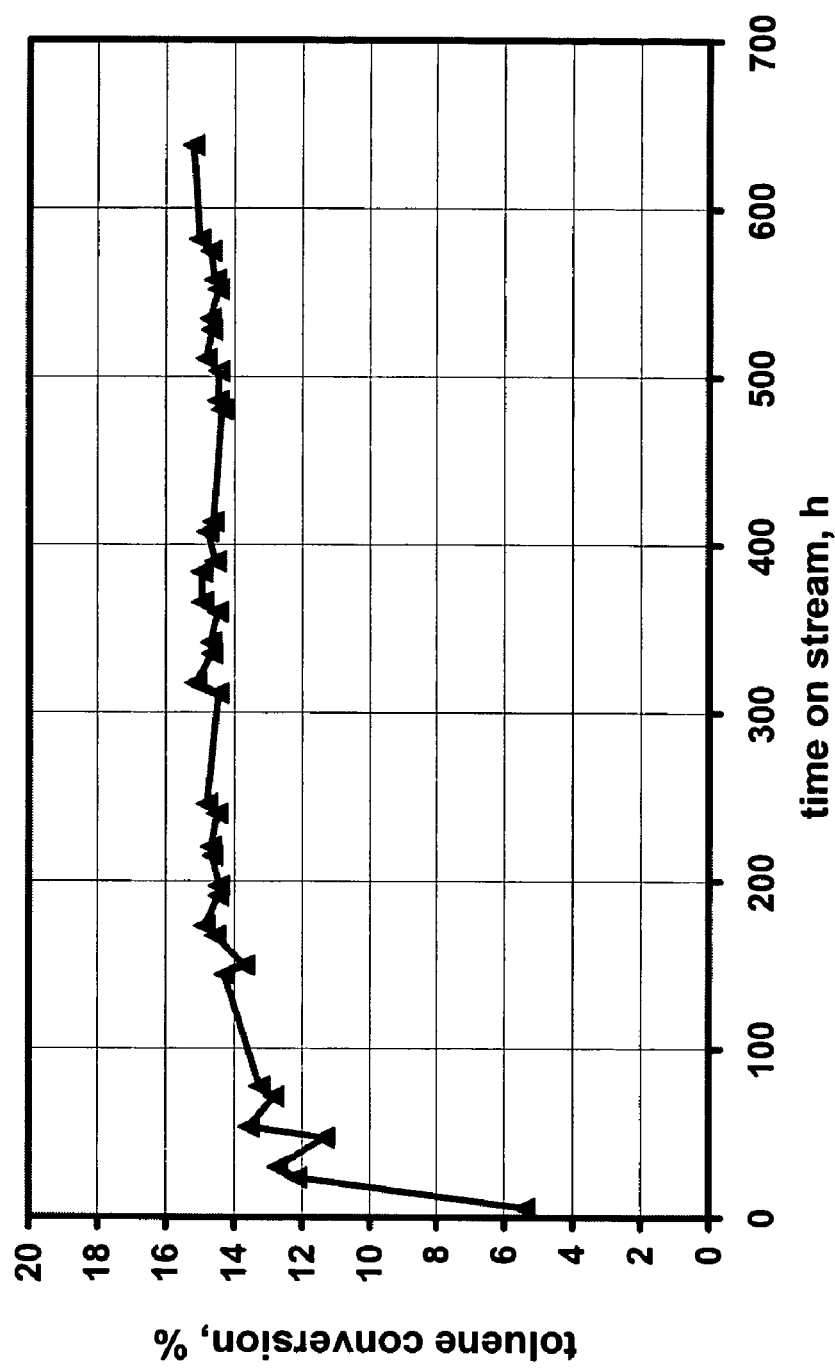
FIG. 4 is a plot of toluene conversion over time for the toluene methylation reaction for Catalyst L of Example 14.
Figure 5:
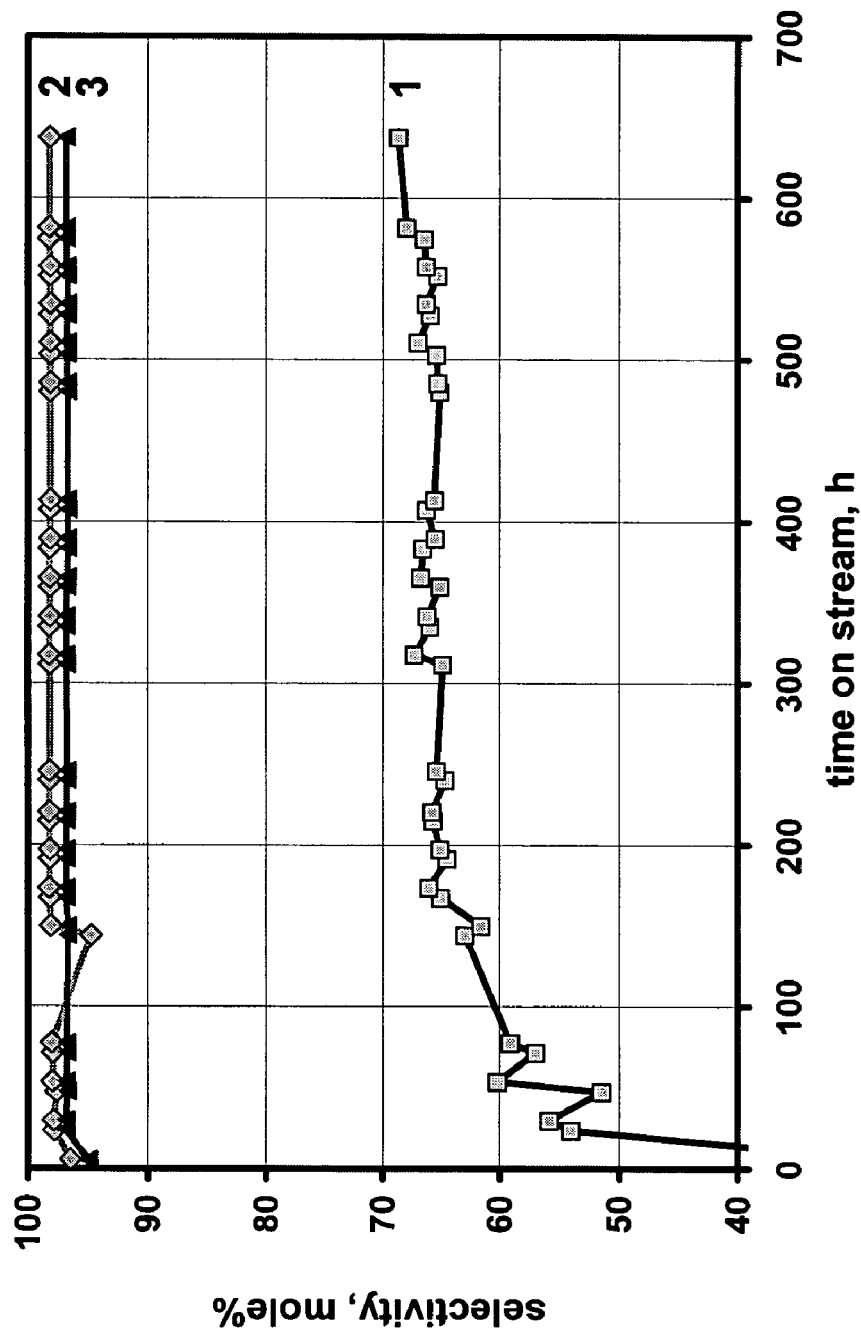
FIG. 5 is a plot of methanol selectivity (curve 1), mixed-xylene selectivity (curve 2) and p-xylene selectivity (curve 3) over time for the toluene methylation reaction for Catalyst L of Example 14.

Catalyst L was further tested for catalyst stability in toluene methylation reaction. The reactor and feed conditions were the same as those described in Examples 1-5. After drying the catalyst at 200° C., the catalyst was steamed overnight at 200° C. A premixed toluene and methanol feed (molar ratio 4.5) was added to the reactor at 200° C. The liquid hourly space velocity (LHSV) (based on methylation feed) was maintained at about 2 hr$^{-1}$ and a cofeed of H$_2$ gas was fed and maintained to provide a H$_2$/methylation feed molar ratio of about 7-8. In addition to H$_2$, water vapor was added to reactor as cofeed. The H$_2$O/methylation feed molar ratio was about 0.8 and the reactor pressure was about 20 psig. The catalyst bed inlet temperature was increased slowly to about 510° C. over a period of time to give toluene conversion of about 14%, and no reactor temperature adjustment was made during the test period of 637 h (26 days). Toluene conversion, and selectivities to mixed xylene, p-xylene and methanol are shown in FIGS. 4 and 5.

Example 15

Figure 6:
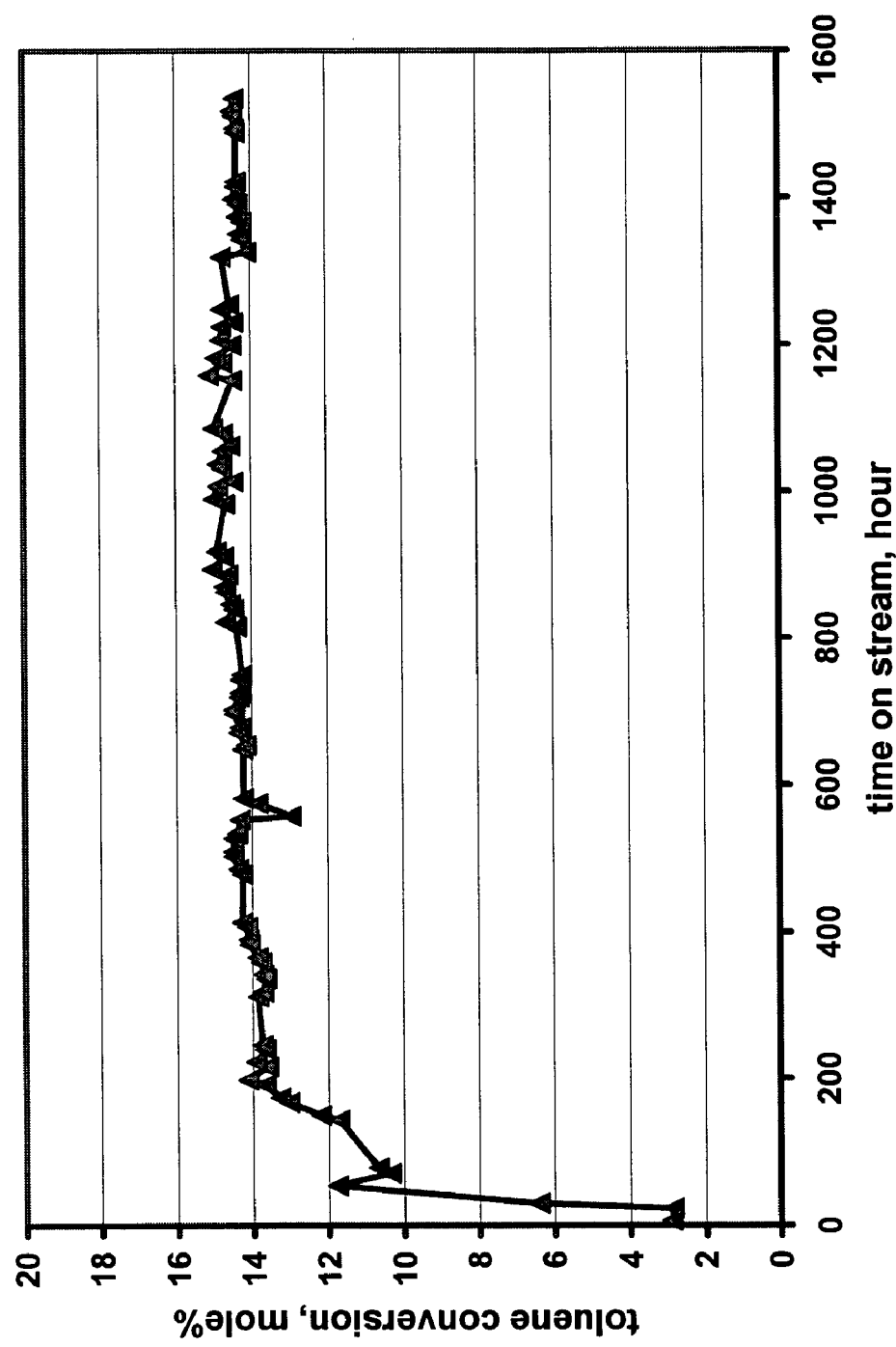
FIG. 6 is a plot of toluene conversion over time for the toluene methylation reaction for Catalyst M of Example 15.
Figure 7:
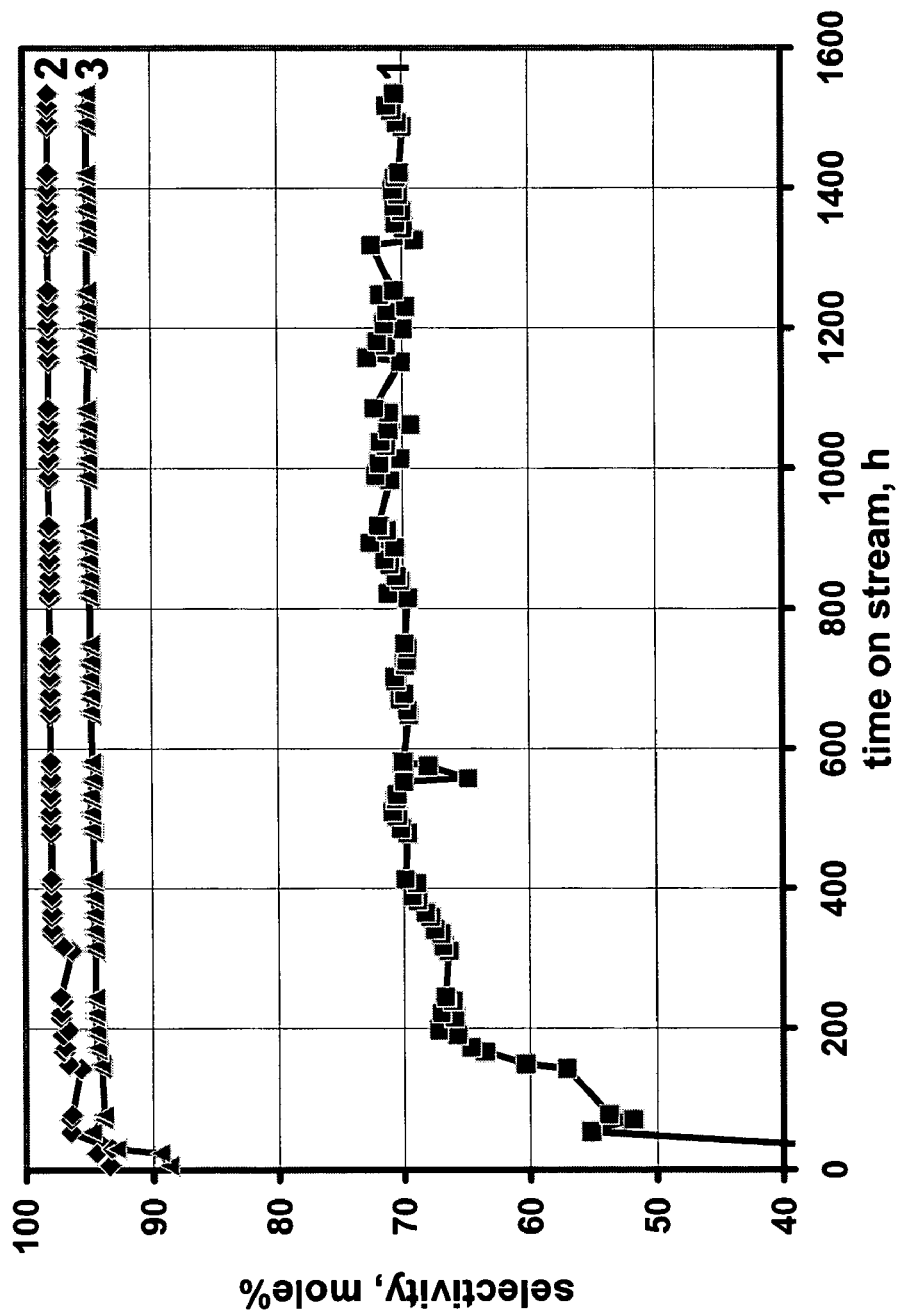
FIG. 7 is a plot of methanol selectivity (curve 1), mixed-xylene selectivity (curve 2) and p-xylene selectivity (curve 3) over time for the toluene methylation reaction for Catalyst M of Example 15.

Catalyst M was further employed to show stable catalytic performances for toluene methylation reaction. The reactor, catalyst charge, catalyst drying and steaming procedure were the same described for Examples 1-5. After drying the catalyst at 200° C., the catalyst was steamed overnight at about 200° C. A premixed toluene and methanol feed (molar ratio 4.5) was added to the reactor at 200° C. The liquid hourly space velocity (LHSV) (based on methylation feed) was maintained at about 2 hr$^{-1}$ and a cofeed of H$_2$ gas was fed and maintained to provide a H$_2$/methylation feed molar ratio of about 7-8. In addition to H$_2$, water vapor was added to reactor as cofeed. The H$_2$O/methylation feed molar ratio was about 0.8 and reactor pressure was about 20 psig. The catalyst bed inlet temperature was increased slowly to 535° C. over a period of time to give toluene conversion of about 14%, and no further reactor temperature adjustment was made during the test period of 1560 h (64 days). Toluene conversion, and selectivities to mixed xylene, p-xylene and methanol are shown in FIGS. 6 and 7.

Example 16

Figure 8:
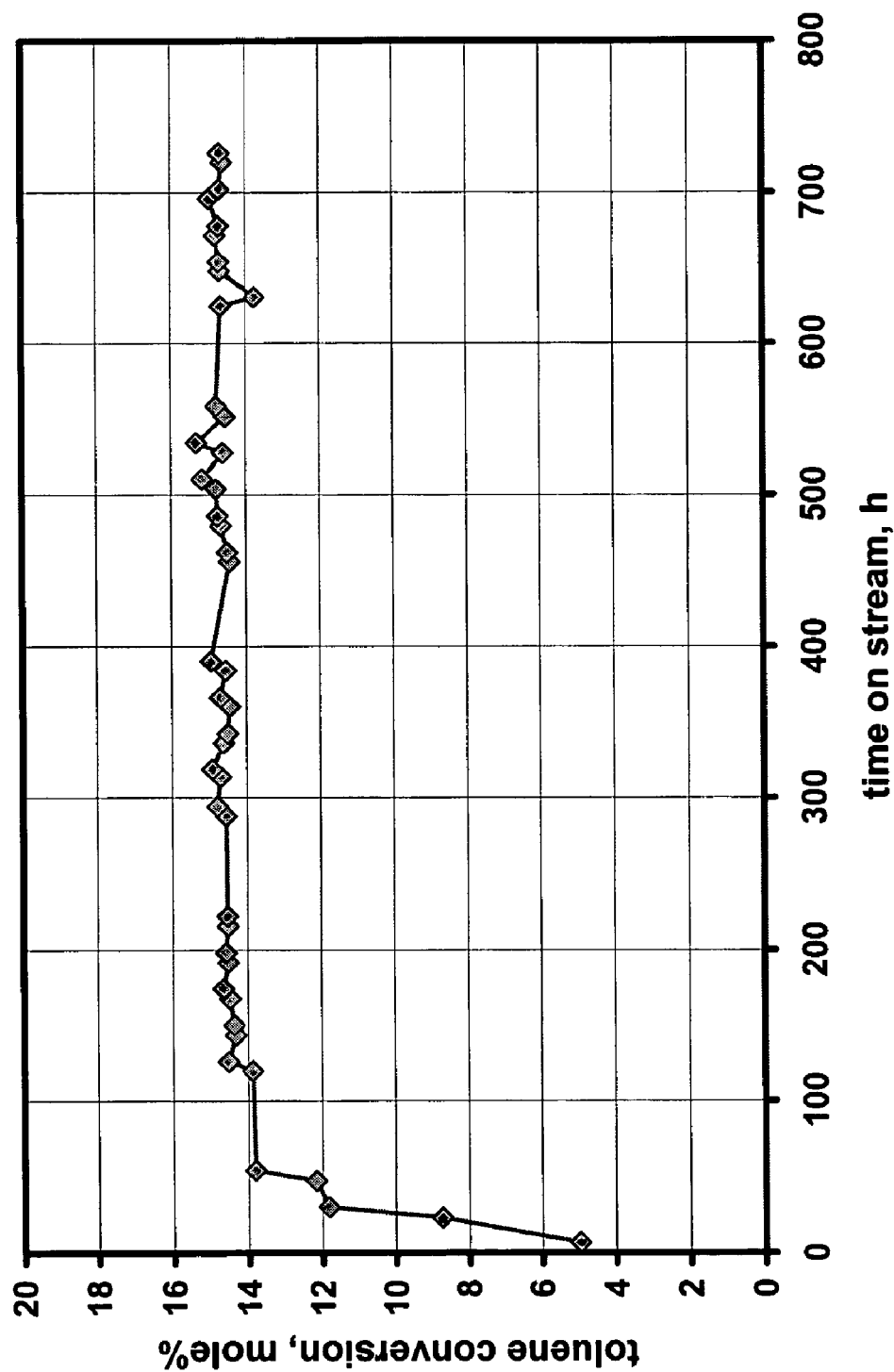
FIG. 8 is a plot of toluene conversion over time for the toluene methylation reaction for Catalyst A of Example 16.

Catalyst A was employed to test its stable activity for toluene methylation. The reactor, feed composition, catalyst drying and steaming conditions were the same as described for Examples 1-5. After drying the catalyst at 200° C., the catalyst was steamed overnight at 200° C. A premixed toluene and methanol feed (molar ratio 4.5) was added to the reactor at 200° C. The liquid hourly space velocity (LHSV) (based on methylation feed) was maintained at about 2 hr$^{-1}$ and a cofeed H$_2$ gas was fed and maintained to provide a H$_2$/methylation feed molar ratio of about 7-8. In addition, water was added to the reactor as cofeed and was vaporized prior to introduction into the reactor. The H$_2$O/methylation feed molar ratio was about 0.8 and the reactor pressure was about 20 psig. The catalyst bed inlet temperature was slowly raised to 492° C. when a toluene conversion of about 14% was obtained and when no further reactor temperature adjustment was made during the test period. Reactor streams were analyzed to calculate conversion and selectivity. FIG. 8 shows steady toluene conversion as a function of time on stream. The unbound P/ZSM-5 catalyst (Catalyst A) showed stable performance during the test period of 726 hours (30 days). Table 11 presents the average toluene conversion, methanol selectivity, mixed-xylene selectivity and p-xylene selectivity for Catalysts A, L and M. Contrasted to the unbound P/ZSM-5 (Catalyst A), the alumina bound catalysts showed at least 5% increased p-xylene selectivity.

TABLE 11

| | Conversion/Selectivity, mole % | | |
|---|---|---|---|
| | Catalyst L Example 14 | Catalyst M Example 15 | Catalyst A Example 16 |
| Toluene Conversion | 14.6 | 14.4 | 14.6 |
| Mixed-Xylene Selectivity | 98.1 | 97.9 | 96.8 |
| p-Xylene Selectivity | 96.7 | 94.8 | 88.0 |
| Methanol Selectivity | 65.7 | 70.0 | 67.7 |

We claim:

1. A method of preparing a zeolite catalyst comprising:
   treating a zeolite with a phosphorus compound to form a phosphorus-treated zeolite;
   heating the phosphorus-treated zeolite to a temperature of about 300° C. or higher;
   combining the phosphorus-treated zeolite with an inorganic oxide binder material to form a zeolite-binder mixture; and
   heating the zeolite-binder mixture at temperature of about 400° C. or higher to form a bound zeolite catalyst.

2. The method of claim 1, wherein:
   the binder material includes at least one of alumina, clay, aluminum phosphate and silica-alumina.

3. The method of claim 1, wherein:
   the binder material is an alumina-containing material.

4. The method of claim 1, wherein:
   the phosphorus-treated zeolite is heated to a temperature of from about 300° C. to about 600° C.

5. The method of claim 1, wherein:
   the zeolite-binder mixture is heated to a temperature of from 400° C. to about 700° C.

6. The method of claim 1, wherein:
   the zeolite is a ZSM-5 zeolite.

7. The method of claim 1, wherein:
   the binder material contains from about 1% to 99% by weight alumina.

8. The method of claim 1, wherein:
   the bound zeolite catalyst exhibits at least two $^{31}$P MAS NMR peaks with maxima at from about 0 to about −55 ppm, with at least one peak having a maximum at from about −40 to about −50 ppm.

9. The method of claim 1, wherein:
   the binder material is present in an amount of from about 1% to about 99% by weight of the bound zeolite catalyst.

10. The method of claim 1, wherein:
    the zeolite contains 10-oxygen ring pores.

11. The method of claim 1, further comprising:
    steaming the bound zeolite at a temperature of 300° C. or less.

12. The zeolite catalyst prepared by the method of claim 1.

13. A method of preparing a zeolite catalyst comprising:
    treating a zeolite with a phosphorus compound to form a phosphorus-treated zeolite having a phosphorus content of from 0.01 to about 0.15 gram of phosphorus per gram of zeolite.
    heating the phosphorus-treated zeolite to a temperature of from about 300° C. to about 600° C.;
    combining the phosphorus-treated zeolite with an alumina or clay binder material to form a zeolite-binder mixture; and
    heating the zeolite-binder mixture at temperature of from about 400° C. to about 700° C. to form a bound zeolite catalyst.

14. The method of claim 13, wherein:
    the zeolite is a ZSM-5 zeolite.

15. The method of claim 13, wherein:
    the binder material contains from about 1% to 99% by weight alumina or clay or their combinations.

16. The method of claim 13, wherein:
    the bound zeolite catalyst exhibits at least two $^{31}$P MAS NMR peaks with maxima at from about 0 to about −55 ppm, with at least one peak having a maximum at from about −40 to about −50 ppm.

17. The method of claim 13, wherein:
    the binder material is present in an amount of from about 1% to about 99% by weight of the bound zeolite catalyst.

18. The method of claim 13, wherein:
    the zeolite contains 10-oxygen ring pores.

19. The method of claim 13, wherein:
    the phosphorus-treated zeolite has a phosphorus content of from 0.07 to about 0.12 gram of phosphorus per gram of zeolite.

20. The method of claim 13, further comprising:
    steaming the bound zeolite at a temperature of 300° C. or less.

21. The zeolite catalyst prepared by the method of claim 13.

22. A zeolite catalyst prepared by treating a zeolite with a phosphorus compound to form a phosphorus-treated zeolite, heating the phosphorus-treated zeolite to a temperature of about 300° C. or higher, combining the phosphorus-treated zeolite with an inorganic oxide binder material to form a zeolite-binder mixture, and heating the zeolite-binder mixture at temperature of about 400° C. or higher to form a bound zeolite catalyst.

23. The catalyst of claim 22, wherein:
    the binder material includes at least one of alumina, clay, aluminum phosphate and silica-alumina.

24. The catalyst of claim 22, wherein:
    the binder material is an alumina-containing material.

25. The catalyst of claim 22, wherein:
    the phosphorus-treated zeolite is heated to a temperature of from about 300° C. to about 600° C.

26. The catalyst of claim 22, wherein:
    the zeolite-binder mixture is heated to a temperature of from 400° C. to about 700° C.

27. The catalyst of claim 22, wherein:
    the zeolite is a ZSM-5 zeolite.

28. The catalyst of claim 22, wherein:
    the binder material contains from about 1% to 99% by weight alumina.

29. The catalyst of claim 22, wherein:
    the bound zeolite catalyst exhibits at least two $^{31}$P MAS NMR peaks with maxima at from about 0 to about −55 ppm, with at least one peak having a maximum at from about −40 to about −50 ppm.

30. The catalyst of claim 22, wherein:
    the binder material is present in an amount of from about 1% to about 99% by weight of the bound zeolite catalyst.

31. The catalyst of claim 22, wherein:
    the zeolite contains 10-oxygen ring pores.

32. The catalyst of claim 22, wherein:
    the bound zeolite is steamed at a temperature of 300° C. or less.

* * * * *